(12) United States Patent
Babineau

(10) Patent No.: US 8,659,421 B2
(45) Date of Patent: Feb. 25, 2014

(54) REMOTE CHILD MONITORING SYSTEM WITH TEMPERATURE SENSING

(75) Inventor: Roger J. Babineau, Taunton, MA (US)

(73) Assignee: Cosco Management, Inc., Wilmington, DE (US)

( * ) Notice: Subject to any disclaimer, the term of this patent is extended or adjusted under 35 U.S.C. 154(b) by 233 days.

(21) Appl. No.: 13/189,130

(22) Filed: Jul. 22, 2011

(65) Prior Publication Data

US 2012/0032797 A1 Feb. 9, 2012

Related U.S. Application Data

(60) Provisional application No. 61/371,430, filed on Aug. 6, 2010.

(51) Int. Cl.
*G08B 1/08* (2006.01)

(52) U.S. Cl.
USPC ............... 340/539.15; 340/693.2; 340/573.2

(58) Field of Classification Search
USPC ............... 340/539.15, 539.1, 573.1, 340/539.25–539.26, 539.3, 539.29, 539.12, 340/693.2
See application file for complete search history.

(56) References Cited

U.S. PATENT DOCUMENTS

| 6,706,002 | B1 * | 3/2004 | Halleck et al. ............... 600/586 |
| 7,740,588 | B1 | 6/2010 | Sciarra |
| 7,774,032 | B2 * | 8/2010 | Swan et al. ............... 455/575.3 |
| 7,973,665 | B2 * | 7/2011 | Desrosiers ............... 340/573.1 |
| 2005/0245839 | A1 * | 11/2005 | Stivoric et al. ............... 600/549 |
| 2006/0017561 | A1 | 1/2006 | Albert |
| 2006/0255936 | A1 * | 11/2006 | Mathews et al. ......... 340/539.15 |
| 2010/0052914 | A1 * | 3/2010 | Tsai ........................... 340/573.1 |

OTHER PUBLICATIONS

International Search Report dated Dec. 12, 2011, for International Application No. PCT/US11/45189.

* cited by examiner

*Primary Examiner* — Daniel Previl
(74) *Attorney, Agent, or Firm* — Barnes & Thornburg LLP

(57) ABSTRACT

The present disclosure relates to a monitoring system for sensing and transmitting sounds in a child's vicinity. The present disclosure relates to a monitoring system for sensing and transmitting indicia of temperature in a child's vicinity and/or of a child.

38 Claims, 5 Drawing Sheets

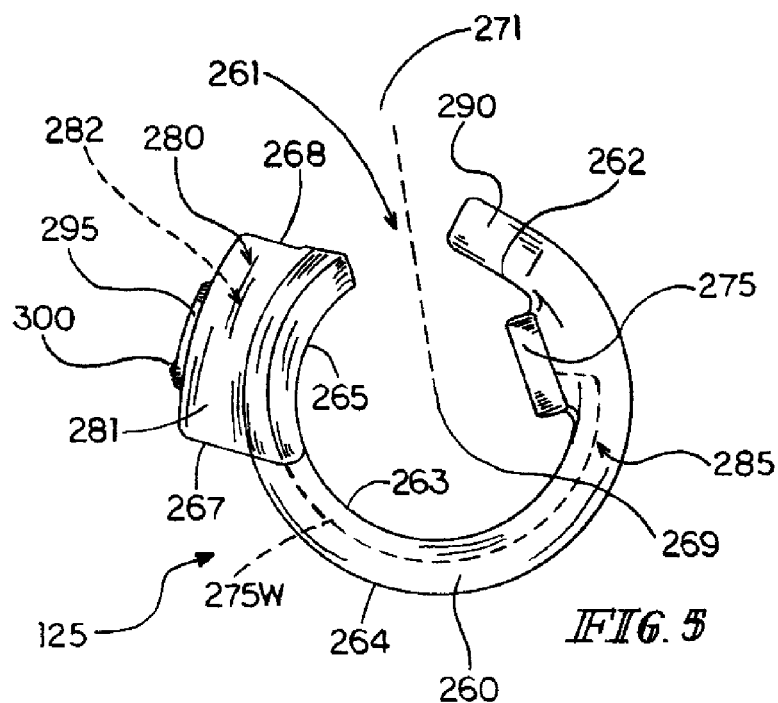
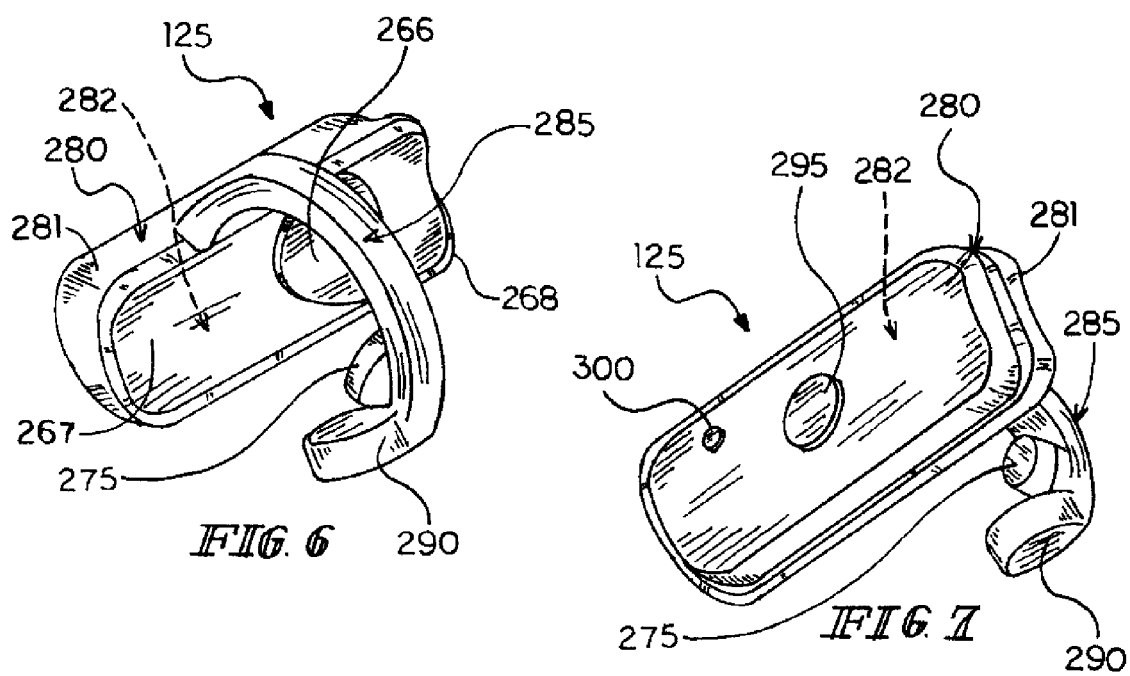

US 8,659,421 B2

REMOTE CHILD MONITORING SYSTEM WITH TEMPERATURE SENSING

PRIORITY CLAIM

This application claims priority under 35 U.S.C. §119(e) to U.S. Provisional Application Ser. No. 61/371,430, filed Aug. 6, 2010, which is expressly incorporated by reference herein.

BACKGROUND

The present disclosure relates to monitoring systems, and particularly to monitor systems that sense and transmit sounds in a vicinity or environment of a child. More particularly, the present disclosure relates to a monitor system that includes sensors that detect a condition of a child.

SUMMARY

According to the present disclosure, a monitoring system is provided for sensing and transmitting sounds. The monitoring system is configured to use the sounds in and around, for example, a child's crib or playyard.

In illustrative embodiments, the monitoring system includes a base unit, a remote parent unit, and a child unit that includes a temperature-sensing underarm band. The system operates in two modes of operation, a first mode, wherein the base unit senses and transmits sounds in a child's vicinity to the remote parent unit and a second mode, wherein the base unit also receives transmitted temperature information sensed by the child unit and transmits that information and/or other indicia indicating that information, such as an alarm, along with ambient temperature information sensed by the base unit to the remote parent unit for output to a parent or other child caregiver via a user interface.

In an embodiment of the present disclosure, the remote parent unit may comprise a user interface that includes both a speaker and a graphic interface that outputs indicia of the sound sensed and transmitted by the base unit and indicia of the temperature data received and/or sensed and transmitted by the base unit. In an embodiment, the base unit of the monitoring system includes a compartment that houses the child unit.

Additional features of the disclosure will become apparent to those skilled in the art upon consideration of the following detailed description of illustrated embodiments exemplifying the disclosure as presently perceived.

BRIEF DESCRIPTION OF THE DRAWINGS

The detailed description particularly refers to the accompanying figures in which:

FIG. 5 illustrates one perspective view of the child unit illustrated in FIG. 1;

FIG. 6 illustrates another perspective view of the child unit illustrated in FIG. 1;

FIG. 7 illustrates another perspective view of the child unit illustrated in FIG. 1;

DETAILED DESCRIPTION

Figure 1:
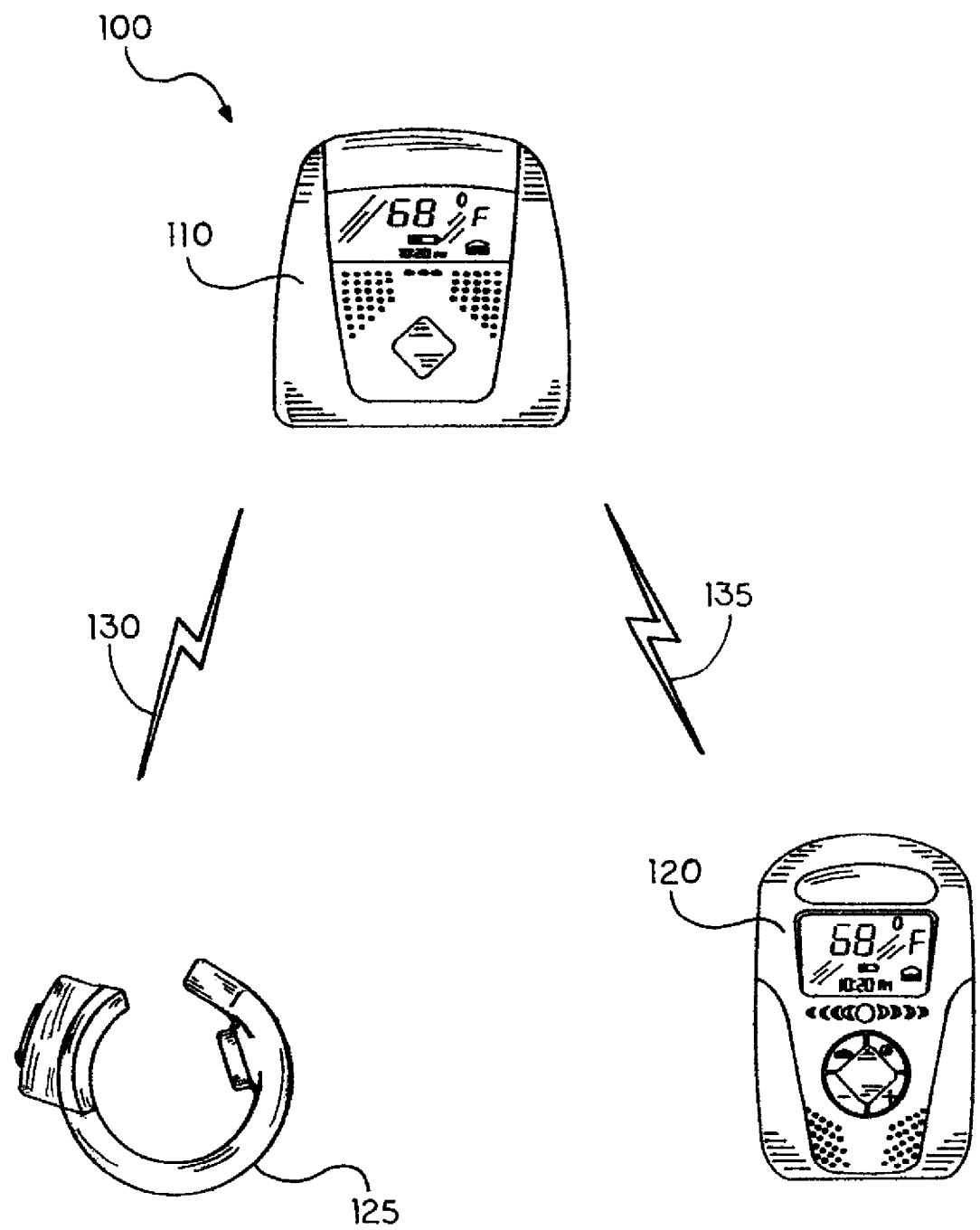
FIG. 1 is an illustrative diagram of the monitoring system in accordance with the present disclosure showing that the monitoring system includes a base unit, a remote parent unit, and a child unit including a temperature-sensing underarm band unit, according to the present disclosure.

At times, great peace of mind for anxious, over-tired parents of small children may result from the ability to monitor the physical well being of a small child. In the instance when the child is ill, monitoring the child's temperature is critical to understanding how sick the child is.

A monitoring system in accordance with the present disclosure operates in two modes of operation, a first mode, wherein the base unit senses and transmits sounds in a child's vicinity to the remote parent unit and a second mode, wherein the base unit also receives transmitted temperature information sensed by the child unit, which may be implemented as a temperature-sensing underarm band fitted under the arm of a child. The base unit may also transmit that received information and/or other indicia indicating that information, along with ambient temperature information sensed by the base unit to the remote parent unit for output to a parent or other child caregiver via a user interface.

Accordingly, an embodiment of the present disclosure includes a monitoring system 100 for monitoring sounds in the vicinity of a child including components, as shown, for example, in FIGS. 1-9. The monitoring system 100 includes a base unit 110, a remote parent unit 120, and a child unit 125. Monitoring system 100, which enables a parent to monitor a child's temperature constantly without having to interfere with their sleep pattern, would have particularly utility and offer some degree of reassurance.

The base unit 110 is configured to communicate with both the child unit 125, along communication link 130 (at, e.g., approximately 313 MHz or the like), and the remote parent unit 120, along communication link 135 (at e.g., approximately 900 MHz, 1.9 GHz, 2.4 GHz, 5.8 GHz, or the like). As a result, the base unit 110 may have a communication range with the remote parent unit 120 of approximately 1,000 feet. In operation, monitoring system 100 is configured to monitor not only the sounds within the vicinity of the child's crib (or other appropriate location) but also, to optionally, monitor the ambient temperature in the vicinity of the child's crib and/or the underarm temperature in real time whether the child is sleeping or awake. This ability to monitor the child's body temperature remotely is provided in a child unit 125 that both senses underarm temperature data for the child and transmits that data to the base unit 110.

The remote parent unit 120 is configured to receive information broadcast from the base unit 110, which information may be in analog or digital format (e.g., DECT-enhanced digital technology). As explained above, that information may include audio signals and/or temperature data indicating the ambient temperature in the child's vicinity and/or the child's body temperature measured by the child unit 125.

The base unit 110 necessarily includes both a receiver and a transmitter or, when combined, a transceiver, that enables the base unit 110 to communicate with both the remote parent unit 120 and the child unit 125. However, as a result of the different frequencies upon which communication links 130 and 135 (see FIG. 1) are implemented, the transceiver and the receiver may be implemented separately to reduce power consumption and manufacturing cost. Along those lines, it is within the scope of this disclosure to reduce the amount of power being consumed during operation of the monitoring system for only auditory sensing in the child's vicinity by turning off the receiver in the base unit 120 when the child unit is not to be used. In this regard, the base unit 110 and/or the remote parent unit 120 may include electronics and functionality that enables a user to select between these modes of operation on the unit(s) themselves.

Although not illustrated, the parent and base units 120, 110 may also include components that enable the selection of multiple transmitting frequencies for the components of the monitoring system 100. Thus, a user may be able to select from a plurality of transmission frequencies for the different communication links 130, 135 illustrated in FIG. 1.

The base unit 110 and remote parent unit 120 may communicate along communication link 135 to function as an audible sound monitoring system, wherein the remote parent unit 120 receives only signals from the base unit 110 that correspond to and enable output of those sounds via the speaker(s) (150 illustrated in FIG. 1) of the remote parent unit. Alternatively, or in addition, the base unit 110 may measure the ambient temperature in the vicinity of the child's crib and transmit data indicating that measured temperature to the remote parent unit for subsequent output via the graphical user interface 140 included in the remote parent unit 120.

The base unit 110 is configured to display optionally that transmitted temperature data received from the child unit 125 and/or ambient temperature measured by a thermometer included in the base unit 110. Additionally, the base unit 110 is further configured to transmit: (1) the received temperature data from the child unit 125 and/or (2) the ambient temperature data measured by the base unit 110 to the remote parent unit 120 for output therefrom.

Figure 2:
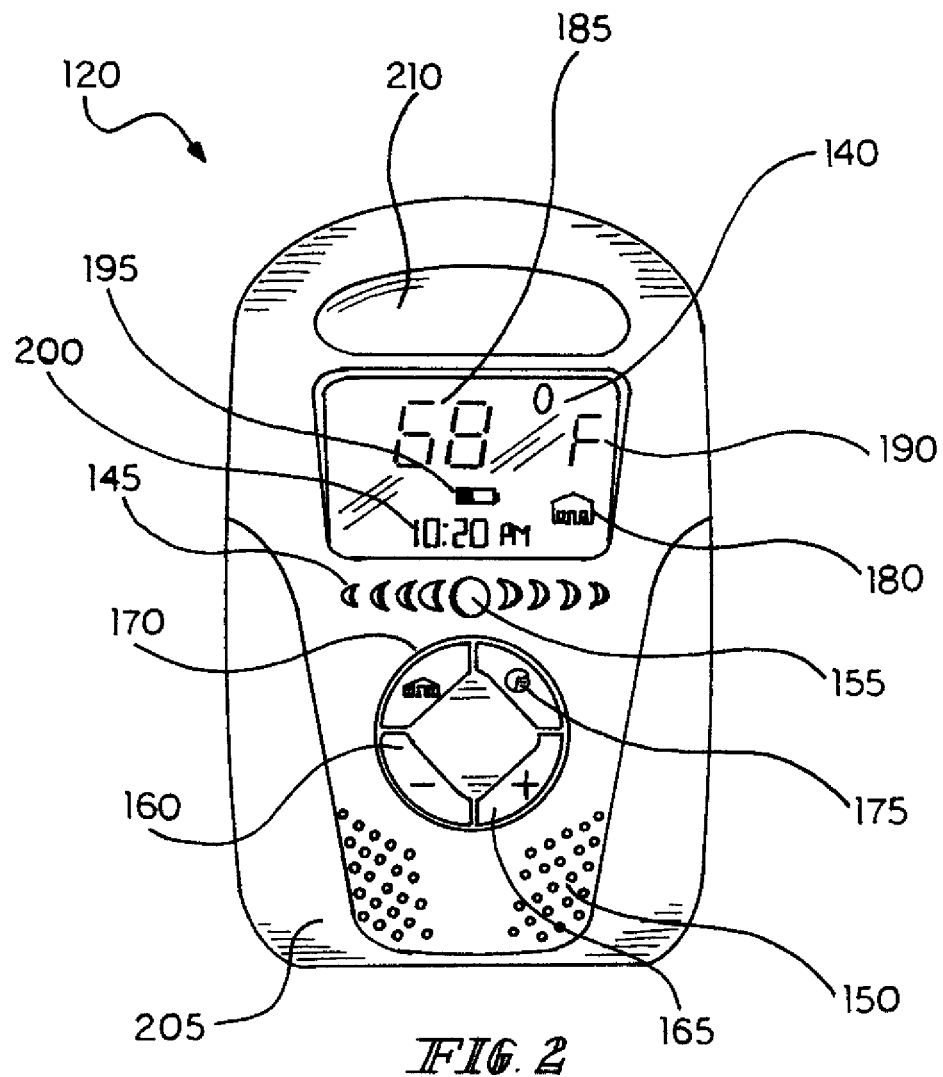
FIG. 2 is a front view of the remote parent unit illustrated in FIG. 1 with additional detail shown.

The remote parent unit 120 is illustrated and described in greater detail in conjunction with FIG. 2. As shown in that figure, the remote parent unit 120 includes various components that enable the output of information and data received from the base unit 110. Accordingly, the remote parent unit 120 includes a graphical user interface 140 that displays various pieces of information to a user. The remote parent unit 120 also includes a plurality of lights 145 which are controlled to light up by electronics located within the remote parent unit 120 in increasing numbers based on the loudness of the sounds sensed by the base unit 110. Thus, the plurality of light sources 145 on the remote parent unit 120 may be configured to function as a noise-level indicator, wherein the level of noise or sound volume in and around the vicinity of the child is indicated by the plurality of light sources which are sequentially and accumulatively lit such that the number of light sources lit illustrate the volume of sound in the vicinity of the child.

In association with the operation of these lights (e.g., light-emitting diodes or some other light-emitting components), the remote parent unit 120 also emits the sounds sensed by the base unit 110 and received from that base unit 110 along the communication link 135. As a result, a user of the remote parent unit 120 is able to output both an auditory indication and a visual indication of the sounds being sensed by the base unit 110.

As shown in FIG. 2, the remote parent unit 120 includes a housing 205 that encloses acoustical means (partially shown as speakers 150, as noted below) and electrical means (not shown) for receiving and outputting the sounds received. Each of these means is well-known and commercially available, and need not be shown.

The housing 205 may further include one or more indicator light sources showing a status of the power condition of the remote parent unit 120. For example, one of the light sources may illuminate green to indicate that at least one battery in the unit 120 charged, one of the light sources may illuminate red to indicate that the power in at least one battery is low. Alternatively, or in addition, one or more light sources may be configured as indicators to indicate the strength of the communication link 135 with the base unit 110.

The housing 205 may further include a switch 155 configured to turn on the remote parent unit 120 as well as various buttons configured to permit a selection of one or more different types of displayed data on the graphical user interface 140 (which may be implemented, e.g., using a Liquid Crystal Display). For example, a user's activation (e.g., pressing of) button 170 will trigger display of the ambient temperature in the child's room as sensed and transmitted by the base unit 110. Likewise, when the monitoring system 100 is in the mode of operation wherein the child unit 125 is sensing and transmitting temperature information, a user's activation (e.g., pressing) of button 175 will trigger display of the temperature sensed by the child unit 125 and re-transmitted by the base unit 110 to the remote parent unit 120.

The switch 155 of the remote parent unit 120 may be activated to turn on/off the remote parent unit. Additionally, buttons 160, 165 may be activated to turn up or down the volume of the outputted sounds from the speaker(s) 150. The speaker(s) 150 shown in FIG. 2, the acoustical means included in the remote parent unit 120 may have openings as illustrated in FIG. 2 that enable the speaker(s) 150 to emit sound.

Because the present disclosure provides a sound monitoring system 100 for sensing, transmitting, and receiving sounds in a child's vicinity, it is within the scope of this disclosure that the remote parent unit 120 acts as a receiver remotely located from the base unit 110, e.g., in a room of a house away from a nursery where the base unit 110 is located. Accordingly, the remote parent unit 120 includes a receiver configured to receive transmitted sounds from the transmitter of the transmitting unit via an antenna (not shown) and output the sound out loud, via the speaker 150. As a result, the receiver may also optionally include a channel selector to select one of at least two frequencies that correspond to a frequency transmitting the sounds from the base unit 110, and a range indicator indicating whether the receiver is within a receiving range of the sounds transmitted by the base unit 110 (note, this range indicator may be implemented on the graphical user interface 140 of the remote parent unit 120). Furthermore, it should be appreciated that the receivers used in the remote parent unit 120 and base unit 110 may include the functionality necessary to scan digitally channels automatically.

The graphical user interface 140 of the remote parent unit 120 also is configured to display the current time of day 200, an indication 190 of whether the displayed temperature 185 is in Fahrenheit or Celsius degrees, an indication 180 of whether the displayed temperature is the ambient temperature in the child's vicinity or the child's temperature measured by the child unit 125, and an indication of battery charge 245.

Figure 3:
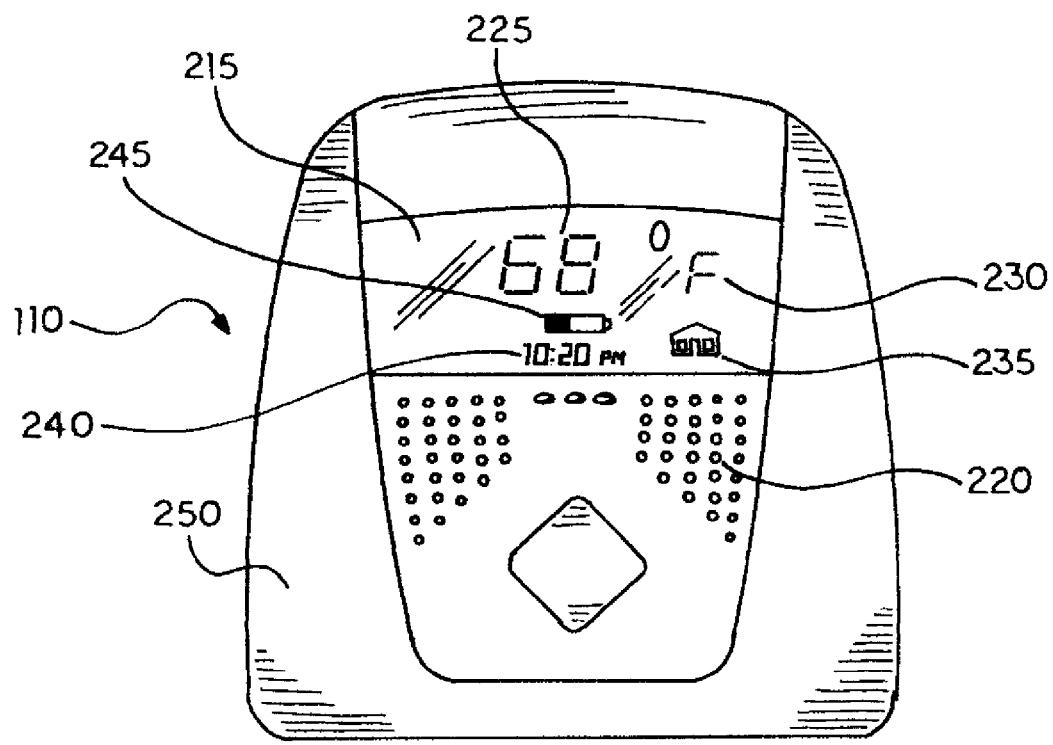
FIG. 3 is a front view of the base unit illustrated in FIG. 1 wherein the transmitter used to retransmit data to the parent unit is enclosed in the housing.

Likewise, as illustrated in FIG. 3, the housing 250 of the base unit 110 includes a graphical user interface 215 (which may be implemented, e.g., using a Liquid Crystal Display) that is configured to display the current time of day 240, an indication 235 of whether the displayed temperature 225 is in Fahrenheit or Celsius degrees, and an indication 235 of whether the displayed temperature is the ambient temperature in the child's vicinity or the child's temperature measured by the child unit 125. In this regard, although not illustrated, the control over whether the ambient temperature or the sensed temperature provided by the child unit 125 is displayed may be determined by a mode of operation set in the child and/or remote parent unit, whether the base unit is receiving data from the child unit 125, etc., and an indication of battery charge 245. The base unit 110 may also include a range indicator indicating whether a receiver configured to receive data from the child unit 125 is within a receiving range of the base unit 110 (note, this range indicator may be implemented on the graphical user interface 215 of the remote parent unit 110).

The housing 250 of the base unit 110 also encloses acoustical means (also termed "means for sensing sound" and partially shown as speakers 220, as noted below) and electrical means (not shown) for sensing and transmitting sounds sensed in the vicinity of the child. As above, each of these means is well-known and commercially available, and need not be shown. The base unit 110 may be mountable, for example, on a railing of a child's crib or rest upon a horizontal surface within the vicinity of the child's crib.

Along with the microphone 220 shown in FIG. 3, the acoustical means included in the base unit 110 may have openings as illustrated in FIG. 3 that enable the microphone 220 to sense or detect the sounds, for example, from a child or from another person or activity in the child's room or area. The acoustical means may include a device or devices, for example, a transmitter having a PC board, mounted, for instance, inside the housing 250, with electrical means configured to convert the acoustically-detected sounds to radio waves to transmit via an antenna also housed in the housing to the remotely-located remote parent unit 120 (which would also include a receiver having an antenna—not shown).

Figure 4:
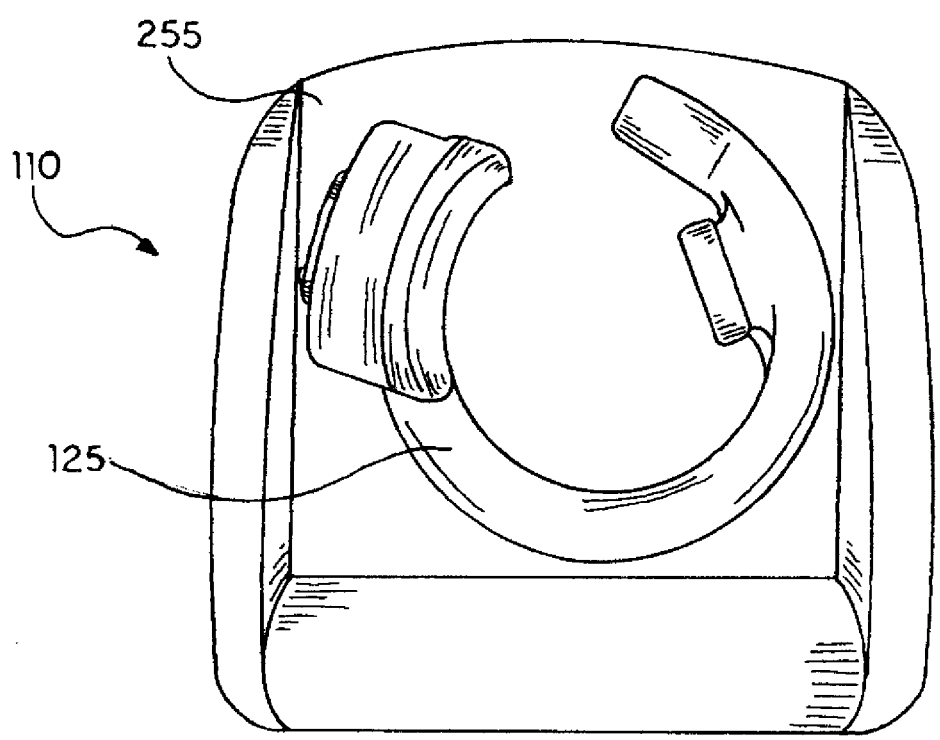
FIG. 4 is a back view of the base unit illustrated in FIG. 1 including at least one compartment provided for housing the child unit including the child unit illustrated in FIG. 1.

Moreover, although not illustrated, the system 100 may be implemented with parent and base units that provide not only sound sensing and transmission and output but may be implemented with video-monitoring capability. Thus, video data may be sensed and transmitted (either in analog or digital) along with digital data associated with a child's temperature. Furthermore, the units may be configured such that the remote parent unit 120 may receive data indicating sounds within the vicinity of the child but may also include a mute button that enables the remote parent unit 120 to turn on lights indicating the presence of sound without actually outputting the sound itself As illustrated in FIG. 4, the back panel of the base unit 110 may be hinged to be partially removable or be configured to be completely removable to provide at least one, and optionally, a plurality of compartments 255 that are configured to hold various attachments or components of the system 100. For example, as illustrated in FIG. 4, compartment 255 may be used to house the child unit 125 when it is not in use to measure the underarm temperature of the child. On the rear of the unit, although not illustrated, a small button is provided that enables a user to toggle back and forth between Fahrenheit and Celsius by pressing the button for some period of time, e.g., two seconds.

The housing 250 may further include one or more indicator light sources showing a status of the power condition of the base unit 110. For example, one of the light sources, may illuminate green to indicate that at least one battery in the unit 110 is charged, one of the light sources may illuminate red to indicate that the power in at least one battery is low. Alternatively, or in addition, one or more light sources may be configured as indicators to indicate the strength of the communication link 130 with the child unit 125 and/or the communication link 135 with the remote parent unit 120.

When the base unit 110 is turned on, an initial icon may be displayed, thereafter a welcome message may be illustrated on the graphical user interface 215. Subsequently, all icons may light up on the graphical user interface along with a backlight (e.g., blue) for some period of time. Subsequently, the base unit 110 will then display time, ambient temperature along with an icon indicating that the ambient temperature is being displayed. In one implementation, if the child unit 125 is on, the base unit will switch the display to display the sensed temperature from the child temperature unit follow a boot up sequence.

As illustrated in FIG. 5, the child unit 125 may be configured to be placed under the arm of the child and attached or placed in the child's arm pit. With this placement complete, the child unit 125 may be operated to monitor the child's temperature as they sleep.

This audible and/or visual alarm may be generated as a result of the child unit 125 sensing a temperature of a particular level and transmitting data to the base unit 110 indicating that temperature level; as a result of the receipt of that data, the base unit 110 may optionally display the measured temperature level on the graphical user display 215 and also transmit that data to the remote parent unit 120. As a result, the remote parent unit 120 may generate the audible and/or visual alarm and, optionally, display the child's measured temperature on the graphical user interface 140 included in the remote parent unit 120.

In at least one implementation of the monitoring system 100, if there is a change in child's monitored temperature as the child sleeps, the parent will be made aware by an audible and/or visual alarm emitted by the remote parent unit 120. For example, an alarm may be triggered at the remote parent unit 110 if the child unit 125 senses the child's body temperature being greater than approximately 101 degrees Fahrenheit or less than approximately 96 degrees Fahrenheit. It is also within the scope of the present disclosure to incorporate other ranges that may be configured in the factory and/or by a user to trigger alarms.

Further, the child unit 125 may be configured to enable real time continuous monitoring of a child's temperature and/or user initiated measurement of the child's temperature remotely from the remote parent unit 120. Accordingly, in such a situation, both the child unit 125 and the base unit 110 would both be operational but a user of the remote parent unit 120 would be able to initiate the sensing of the child's temperature.

As illustrated in FIGS. 5-7, the child unit 125 includes an armband sensor 275, a comfort-fit band 285, and a housing 280. Housing 280 includes an outer shell 281 and electric components 282 located inside outer shell 281. Armband sensor 275 is configured to sense the body temperature of a child wearing child unit 125. Alternatively, such a temperature sensor could be included in electric components 282 located inside outer shell 281 of housing 280. Comfort-fit armband 275 is configured to hold one or more temperature sensors in place to provide sensor to skin contact and enable temperature sensing. These sensors are coupled electronically to the transmitter included in housing 280 using any suitable means.

Located on the exterior of the housing 300 is an on/off button 295 that controls operation of the child unit 125 when actuated (in, for example, a toggle button manner). The exterior of the housing 300 also includes a light source 300 (e.g., light-emitting diode(s)) that indicates the operation of the child unit 125. Optionally, the light source 300 may also be controlled to indicate (e.g., blinking or dimmed light emission) when a power source (e.g., battery, not shown) within the unit 125 requires recharging or replacement. Because both the base unit 110 and remote parent unit 120 are both implemented using conventional technology, both units may include power jacks (not shown) to receive power from a direct current source (not shown). The child unit 125 may also include a power source (e.g., a battery) that may be similarly rechargeable and/or rechargeable by interaction with the base unit 110. The power source is included in electric components 282 located in outer shell 281 of housing 280 in an illustrative embodiment.

As explained above, the child unit 125 may be configured to sense the temperature of the child and transmit radio frequency broadcast signals including data regarding that temperature to the base unit 110. This information may be displayed directly on the base unit 110 and sent again via RF to the remote parent unit 120. In turn that data may be directly displayed on the graphical user interface 140 and/or used to generate audio and/or visual alarm emanating from the remote parent unit 120.

Although not shown, the child unit 125 may include electronics that enable the calibration of the unit 125 in electric components 282. Thus, a user may place the child unit 125 on the child's arm approximately twenty minutes before bedtime to allow the unit to calibrate to the skin temperature. The graphical user interface 215 on the base unit 110 may display some indicia of the progress of the calibration; subsequently, the base unit 110 may issue an alarm, e.g., a beep, to communicate that the child unit 125 is calibrated to the child's skin temperature at the arm band. Once calibrated, the base unit 110 may be configured to then switch between the temperature sensed by the unit 125 and the ambient temperature at a prescribed interval, e.g., five seconds.

The child-unit 125 may include more than one temperature-measurement sensor located apart from one another and electronics that enable comparison of the sensed temperatures provided by those sensors. This redundancy enables the child unit 125 to generate an alarm and/or transmit data to the base unit 110 indicating that one of the sensors may not be accurately sensing the temperature of the child. Such information may be useful in diagnostics for determining proper operation of the unit 125 and/or proper placement of the unit 125 in the armpit of the child. As a result, such information may trigger a visual error message displayed on the base unit 110 as well as the transmission of corresponding error message data to the remote parent unit 120 for generation and output of a visual and/or audible alarm.

The components of the monitoring system 100 provide monitoring of a child's temperature in a manner that is a minimally invasive, minimally disruptive to their sleep pattern, and provides the ability to monitor the child's temperature on a continuous, real time basis. Additional utility is provided in that the monitoring system 100 is implemented in large part in conjunction with a product already commonly used in the child room environment, a conventionally known audio child monitor. As a result, the system provides the utility of an every day appliance while also providing a critical tool to monitoring child health.

The various components of the monitoring system 100, e.g., the base unit 110, remote parent unit 120, and child unit 125 may each include at least one battery, which may be located in the housings 250, 205, 280. These batteries may be rechargeable and/or replaceable or not rechargeable but still replaceable. Accordingly, each of the components of monitoring system 100 may further include charging contacts (not shown), the contacts being adapted to re-energize the rechargeable batteries when contacts are mated with contacts on a charger (not shown).

The child unit 125 includes a housing 280, a comfort-fit band 285, and an armband sensor 275 as shown, for example, in FIGS. 5-9. The child unit 125 is adapted to be worn by a child and is thus separated physically from the base unit 110 and the remote parent unit 120 as suggested in FIG. 1.

Figure 8:
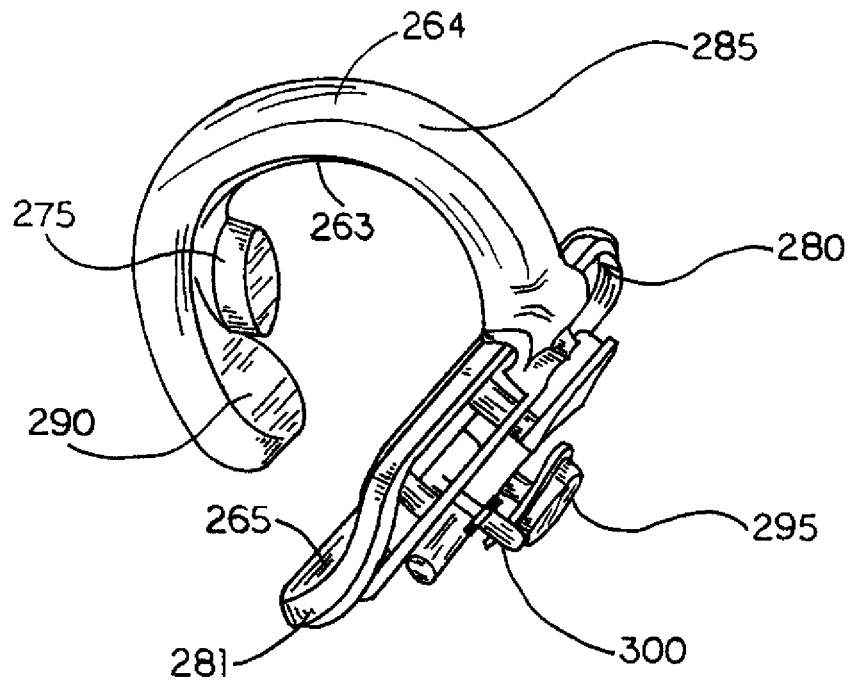
FIG. 8 illustrates another perspective view of the child unit illustrated in FIG. 1 with internal components of the underarm unit exposed.
Figure 9:
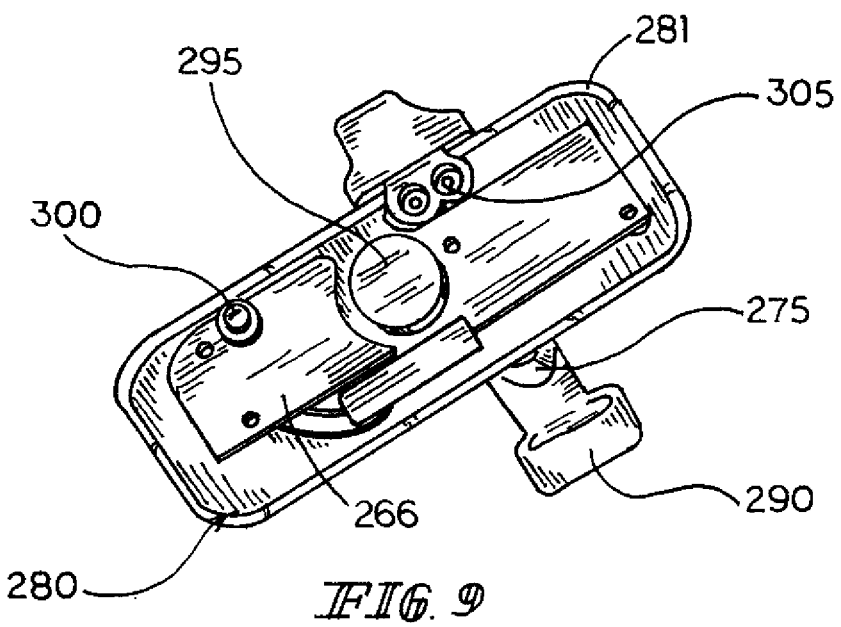
FIG. 9 illustrates another perspective view of the child unit illustrated in FIG. 1 with internal components of the underarm unit exposed.

The housing 280 of the child unit 125 includes electronic components 282 that are contained within the outer shell 281 and are configured to: (1) sense the temperature of the child when the unit is operating and (2) transmit data from the unit 125 to the base unit 110 for subsequent display, potential analysis, and re-transmission to the remote parent unit 120. Armband sensor 275 may also comprise a temperature sensor. As such, the child unit 125 may include the above-described temperature sensor(s) as well as a transmitter for transmitting the sensed temperature information or some associated indicia (e.g., a status message including a normal status message, an alarm status message, etc.) to the base unit 125. Such components (as illustrated in FIGS. 8 and 9) and associated hardware may be included in the housing, a cover of which being secured using, for example, a plurality of screws inserted in screw apertures 305 as illustrated in FIG. 9. The housing 280 further comprises an arm stabilizer 266 coupled to the outer shell 281 of the housing 280 at a location between a first end 267 of the housing 280 and a second end 268 of the housing 280, as illustrated in FIG. 6.

The child unit 125 further includes a comfort-fit band 285 which is comprised of a distal end 290 and a bridge 260 as suggested in FIGS. 5 and 6. The bridge 260 is configured to connect the armband sensor 275 to the outer shell 281 of the housing 280 at a location between the first end of the housing 267 and the arm stabilizer 266. The bridge 260 comprises a concave inner side 263 wherein a portion of the inner side 263 faces toward the housing 280. The bridge 260 further comprises a convex outer side 264 wherein a portion of the outer side 264 faces away from the housing 280. It is within the scope of this disclosure to couple armband sensor 275 to electric components 282 located in outer shell 281 of housing 280 electrically using wires 275W extending through bridge 260.

The distal end 290 of the comfort-fit band 285 is cantilevered from the bridge 260, extending in a direction towards the housing 280, and has a flat inner surface 262. The distal end 290 is spaced apart from the housing 280, resulting in a space 261 between the distal end 290 and the housing 280 as suggested in FIG. 5. This space 261 is adapted to accept a child's arm such that the child's arm passes through the space 261 in a direction towards the bridge 260.

The child unit 125 is further adapted to be worn on the arm of a child by assuming a semi-circular shape. This semi-circular shape is created as the angle of curvature of housing 280 is approximately equal to the radius of curvature of the bridge 260. The distal end 290 may also have an approximately equal radius of curvature or may protrude at a constant angle from the bridge 260. An exemplary embodiment of the child unit 125 comprises the armband sensor 275 occupying an arc length of 57 degrees multiplied by half of the furthest distance between a point on the inner side of the comfort fit band 263 and a point on the inner side 265 of the housing 280. An exemplary embodiment of the child unit 125 further comprises an arc length of the bridge 260 of 192 degrees multiplied by half of the furthest distance between a point on the concave inner side 263 of the comfort-fit band 285 and a point on the inner side 265 of the housing 280.

A grid, as illustrated in FIG. 5, may be developed in the following manner. The origin of the grid is located at the point 269 exactly halfway between the longest distance between a point on the inner surface 263 of the comfort-fit band 285 and the inner surface 265 of the housing 280. The reference line 271, or the line of 0 degrees, is drawn by extending a line upwards, as illustrated in FIG. 5. The armband sensor 275 occupies the arc segment between approximately 55 and 110 degrees away from reference line 271. The bridge 260 occupies the arc segment between approximately 53 degrees and 245 degrees away from reference line 271.

The child unit 125 further includes an armband sensor 275 located on the concave inner side of the bridge 260. The armband sensor 275 is further positioned to face any part of the child unit 125 to promote contact with the skin on the arm of a child and at least one temperature-sensing sensor included in the armband sensor 275.

The disclosed monitoring system senses and transmits sounds, skin temperature, and/or ambient temperature in a child's vicinity by employing a base unit 110, a remote parent unit 120, and a child unit 125, as shown in FIG. 1. Child unit 125 is adapted to be worn by a child.

The base unit 110 is designed to be placed in the vicinity of the child and serves a plurality of purposes. One service facilitated by the base unit 110 is the ability to transmit sound data to the remote parent unit 120. This is accomplished by employing the housing 250 to enclose a microphone and transmitter, wherein the microphone is configured to detect the sounds in the vicinity of the child and the transmitter is configured to transmit associated sound data indicating those sounds, as shown in FIG. 3.

A second, optional service facilitated by the base unit 110 is the ability to sense and transmit ambient temperature data to the remote parent unit 120. The base unit 110 employs at least one temperature sensor to gather ambient temperature data, and then uses the transmitter enclosed in the housing 250 to transmit data indicating the ambient temperature to the remote parent unit along with the sound data, as shown in FIG. 3. The base unit 110 may also display the ambient temperature 225 on the graphical user interface 215, as shown in FIG. 3.

Communication between the base unit 110 and the remote parent unit 120 is done wirelessly, and facilitated by the at least one of a transmitter and a receiver enclosed in the housing 250 of the base unit 110, as shown in FIG. 3. This wireless communication may take place at one of approximately 313 MHz, 900 MHz, 1.9 GHz, 2.4 GHz, and 5.8 GHz.

The remote parent unit 120 is designed to allow a parent to monitor his or her child from a remote area to the base unit 110. The remote parent unit 120 accomplishes this by including a housing 205 adapted to enclose a receiver configured to receive the sound data transmitted by the base unit 110. An indication of the sensed sounds based on the received sound data is then outputted by the onboard speakers 150, which are also enclosed in the housing 205, as shown in FIG. 2. The onboard graphical user interface 140 may also be used to output a visual indication of the sound data, as shown in FIG. 2.

The volume level of the speakers 150 of the remote parent unit 120 is customizable. Buttons 160 and 165 coupled to the remote parent unit 120 may be used to control the volume of the speakers 150. A visual indication of the volume is given to a user by employing the plurality of lights 145 included on the remote parent unit 120, as shown in FIG. 2. The plurality of lights 145 are configured to turn on sequentially as an indication of an increase in volume level, and a decrease of volume level is indicated by the plurality of lights 145 sequentially turning off. In the case where the volume is completely off (i.e. muted), the remote parent unit 125 would continue to output a visual indication of the sound data through the graphical user interface 140 and/or the plurality of lights 145, as shown in FIG. 2.

The transmitter included on the remote parent unit 120 is also adapted to receive temperature data from the base unit 110. Temperature data may include ambient temperature data from the base unit 110, or temperature data from the child-unit 125 originally sent to the base unit 110, and then retransmitted to the remote parent unit 120, as shown in FIG. 1. The remote parent unit 120 is equipped to output an indication of the temperature data 185 on the onboard graphical user interface 140, as shown in FIG. 2.

In the case where a child is sick, it is extremely useful for a parent to be alerted whenever a child's temperature deviates from a certain zone. The monitoring system is able to address this issue by employing the remote parent unit 120 to output an alarm through onboard speakers 150, as shown in FIG. 2. An alarm would sound based on temperature data measured by the child unit 125, which is received by the base unit 110 and retransmitted to the remote parent unit 120, as shown in FIG. 1. This feature is enhanced by allowing a user to customize the zone where a deviation of temperature from the zone would result in an alert.

The child unit 125 is designed to gather temperature data from a child, and transmit the temperature data to the base unit 110. Temperature data is gathered from a child by gathering sensor data from at least one sensor included on the armband sensor 275. The armband sensor 275 is able to gather temperature data continually as it is kept in contact with the child's skin. This is made possible by employing the comfort-fit band 285 to secure the child unit 125 to the arm of a child, as shown in FIG. 6. The comfort fit band 285 may also be a flexible armband. The child unit 125 is able to communicate the temperature data with the base unit 110 by employing at least one of a transmitter and a receiver enclosed in the housing 280, as shown in FIG. 9.

The monitoring system may operate in two modes of operation, a first mode, wherein the base unit 110 senses and transmits sound data in a child's vicinity to the remote parent unit 120 and a second mode, wherein the base unit 110 also receives the child temperature data transmitted by the child unit 125 and re-transmits that data along with ambient temperature data sensed by the base unit 110 to the remote parent unit 120 for output via a user interface, as shown in FIG. 1. In the first mode, the receiver of the base unit may be off. In the second mode, however, the receiver is on as it facilitates the constant transmission of temperature data from the child unit 125 to the base unit 110.

The parent unit 120 and base unit 110 may also include at least one rechargeable battery, enabling the units to be used away from an electrical outlet. The parent unit 120 and base unit 110 may include a rechargeable battery and charging contacts to re-energize the at least one rechargeable battery included within the housings of the respective units when mated with a respective charger. The child unit 125 may also include at least one rechargeable battery that is configured to be rechargeable when the base unit is charged. As shown in FIG. 4, the child unit is adapted to be stored in the plurality of compartments 255 of the base unit 110.

Although the present disclosure has been described and illustrated in detail, it is to be clearly understood that this is done by way of illustration and example only and is not to be taken by way of limitation. The spirit and scope of the present disclosure are to be limited only by the terms of the appended claims.

The invention claimed is:

1. A monitoring system for sensing and transmitting sounds in a child's vicinity, and sensing and transmitting data indicating a measured ambient temperature in the child's vicinity and/or a measured temperature of the child, the monitoring system comprising
a base unit comprising a housing enclosing a microphone configured to detect the sounds in the child's vicinity and a transmitter configured to transmit associated sound data indicating those sounds;
a remote parent unit comprising a housing enclosing a receiver configured to receive the sound data transmitted by the base unit and a speaker configured to output an indication of the sensed sounds based on the received sound data, and
child unit means for measuring a temperature of the child and transmitting associated temperature data indicating the measured child temperature to the base unit,
wherein the base unit includes means for receiving the temperature data indicating the measured child temperature and retransmitting said temperature data to the remote parent unit.

2. The monitoring system of claim 1, wherein the base unit further comprises a sensor configured to measure the ambient temperature in the child's vicinity and the transmitter of the base unit is configured to transmit the data indicating the ambient temperature to the remote parent unit along with the sound data.

3. The monitoring system of claim 1, wherein the child-unit means includes at least one of a transmitter and a receiver for communicating with the base unit.

4. The monitoring system of claim 1, wherein the child-unit means includes a sensor configured to sense an underarm temperature of the child and an armband attached to the sensor and configured to enable the sensor to be attached to the child.

5. The monitoring system of claim 1, wherein the remote parent unit is configured to output an indication of the received sound data.

6. The monitoring system of claim 1, wherein the remote parent unit is configured to output an indication of the ambient temperature in the child's vicinity and/or the temperature data sensed by the means for measuring the temperature of the child.

7. The monitoring system of claim 1, wherein the base unit further comprises a microphone configured to detect the sounds in the child's vicinity.

8. The monitoring system of claim 1, wherein the remote parent unit speaker outputs at least one alarm based on the child's temperature measured by the child unit means, which is received by the base unit and re-transmitted to the remote parent unit.

9. The monitoring system of claim 1, wherein the remote parent unit and base unit communicate with one another at one of approximately 900 MHz, 1.9 GHz, 2.4 GHz, and 5.8 GHz.

10. The monitoring system of claim 1, wherein the base unit includes at least one of a transmitter and a receiver for communicating with the child-unit means.

11. The monitoring system of claim 1, wherein the base unit and the child-unit means communicate with one another at approximately 313 MHz.

12. The monitoring system of claim 1, wherein the remote parent unit includes a visual indication of a volume level of sounds sensed in the child's vicinity based on the sound data received from the base unit.

13. The monitoring system of claim 12, wherein the visual indication of the volume level comprises a plurality of light sources configured to turn on sequentially as an indication of an increase in volume level.

14. The monitoring system of claim 12, wherein the visual indication of the volume level cooperates with the speaker of the remote parent unit optionally to mute sound output from the speaker while indicating volume level via the visual indication of the volume level.

15. The monitoring system of claim 1, wherein the child-unit means includes a plurality of temperature-sensing sensors.

16. The monitoring system of claim 1, wherein the remote parent unit is configured to issue an audible alert when a temperature measured by the child-unit means falls below or rises above a set range.

17. The monitoring system of claim 16, wherein the set range is configurable by a user.

18. The monitoring system of claim 1, wherein the child-unit means is configured to measure continuously the child's temperature and transmit the associated temperature data to the base unit.

19. The monitoring system of claim 1, wherein each of the parent and base units includes at least one rechargeable battery and charging contacts to re-energize the at least one rechargeable battery included within the housings of the respective units when mated with a respective charger.

20. The monitoring system of claim 1, wherein the child-unit means includes a housing, an armband sensor, and a band arranged to interconnect the housing and the armband sensor to provide means for retaining the housing and the armband sensor on the arm of a child wearing the child-unit means.

21. The monitoring system of claim 20, wherein the armband sensor includes a temperature sensor configured to measure the temperature of a child wearing the child-unit means and the housing includes an outer shell formed to include an interior region and an electronic system lying in the interior region and comprising a data transmitter configured to transmit the associated temperature data indicating the measured child temperature measured by the temperature sensor in the armband sensor.

22. The monitoring system of claim 21, wherein the band includes a bridge coupled to and arranged to extend between the housing and the armband sensor and the bridge includes a concave inner surface adapted to face toward an arm of a child wearing the child-unit means on said arm.

23. The monitoring system of claim 22, wherein the band further includes a distal end cantilevered to the bridge at the armband sensor and arranged to extend away from the bridge.

24. A monitoring system for sensing and transmitting sounds in a child's vicinity, and sensing and transmitting data indicating a measured ambient temperature in the child's vicinity and/or a measured temperature of the child, the monitoring system comprising
a base unit comprising a housing enclosing a microphone configured to detect the sounds in the child's vicinity, a temperature sensor configured to measure the ambient temperature in the child's vicinity, and a transmitter configured to transmit sound data indicating the detected sounds and data indicating the measured ambient temperature;
a remote parent unit comprising a housing enclosing a receiver configured to receive the data transmitted by the base unit and a speaker configured to output an indication of the sensed sounds based on the received sound data, and a child unit comprising a housing coupled to a flexible armband and including a temperature sensor configured to measure the temperature of the child and a transmitter configured to transmit data indicating the measured child temperature to the base unit, wherein the base unit further includes a receiver configured to receive the child temperature data from the child unit, and wherein the transmitter of the base unit is further configured to re-transmit the received child temperature data along with the ambient temperature data and sensed sound data to the remote parent unit.

25. The monitoring system of claim 24, wherein the system operates in two modes of operation, a first mode, wherein the base unit senses and transmits sound data in a child's vicinity to the remote parent unit and a second mode, wherein the base unit also receives the child temperature data transmitted by the child unit and re-transmits that data along with ambient temperature data sensed by the base unit to the remote parent unit for output via a user interface.

26. The monitoring system of claim 25, wherein, in the first mode, the base unit senses and transmits the ambient temperature data sensed by the base unit to the remote parent unit for display via a user interface.

27. The monitoring system of claim 25, wherein, in the first mode, the receiver of the base unit is off.

28. The monitoring system of claim 25, wherein, in the second mode, the child unit is configured to transmit continuously the measured child temperature data to the base unit.

29. The monitoring system of claim 24, wherein the speaker of the remote parent unit outputs at least one alarm based on the child's temperature data transmitted to the base unit and re-transmitted from the base unit to the remote parent unit.

30. The monitoring system of claim 24, wherein the remote parent unit and base unit communicate with one another at one of approximately 900 MHz, 1.9 GHz, 2.4 GHz, and 5.8 GHz.

31. The monitoring system of claim 24, wherein the base unit and child unit communicate with one another at approximately 313 MHz.

32. The monitoring system of claim 24, wherein the remote parent unit includes a plurality of light sources configured visually to indicate a volume level of sounds detected by the base unit by sequentially turning on as an indication of an increase in volume level.

33. The monitoring system of claim 32, wherein the remote parent unit is configured optionally to mute sound output from the speaker while indicating volume level via the plurality of light sources.

34. The monitoring system of claim 24, wherein the speaker of the remote parent unit is configured to issue an audible alert when the measured child temperature falls below or rises above a set range.

35. The monitoring system of claim 34, wherein the set range is configurable by a user.

36. The monitoring system of claim 24, wherein the child unit includes a plurality of temperature-sensing sensors.

37. The monitoring system of claim 24, wherein each of the parent and base units includes at least one rechargeable battery and charging contacts to re-energize the at least one rechargeable battery included within the housings of the respective units when mated with a respective charger.

38. The monitoring system of claim 37, wherein the child unit includes at least one rechargeable battery that is configured to be rechargeable when the base unit is charged.

* * * * *